United States Patent [19]

Reinhart et al.

[11] Patent Number: 4,750,496

[45] Date of Patent: Jun. 14, 1988

[54] METHOD AND APPARATUS FOR MEASURING BLOOD GLUCOSE CONCENTRATION

[75] Inventors: Richard Reinhart, Lawrenceville, N.J.; Fred Letterio, Philadelphia, Pa.; Peter Pugliese, Bernville, Pa.; Carl Ritter, Aldan, Pa.; Glenn Lubrano, Metairie; Jerry Guilbault, Slidell, both of La.; Christopher Feistel, Laguna Beach, Calif.

[73] Assignee: Xienta, Inc., Bernville, Pa.

[21] Appl. No.: 7,776

[22] Filed: Jan. 28, 1987

[51] Int. Cl.[4] .............................................. A61B 5/00
[52] U.S. Cl. .................................... 128/635; 204/403; 204/415; 204/431
[58] Field of Search ................ 128/635; 204/403, 415, 204/431

[56] References Cited

U.S. PATENT DOCUMENTS

| | | | |
|---|---|---|---|
| 4,535,778 | 8/1985 | Kitralakis et al. | 128/635 |
| 4,650,547 | 3/1987 | Gough | 128/635 X |
| 4,671,288 | 6/1987 | Gough | 128/635 |

FOREIGN PATENT DOCUMENTS 2816519 10/1979 Fed. Rep. of Germany ...... 128/635

*Primary Examiner*—Lee S. Cohen
*Attorney, Agent, or Firm*—Gottlieb, Rackman & Reisman

[57] ABSTRACT

A non-invasive method for measuring blood glucose concentration using glucose present at the mucosal surface of a living being is provided. The method includes the steps of positioning a glucose oxidase membrane on the mucosal surface, providing oxygen for peroxidative oxidation of the glucose present thereat, electrically measuring the amount of hydrogen peroxide product and calibrating that amount to determine blood glucose concentration. Also provided are electrode devices suitable for carrying out the method.

41 Claims, 7 Drawing Sheets

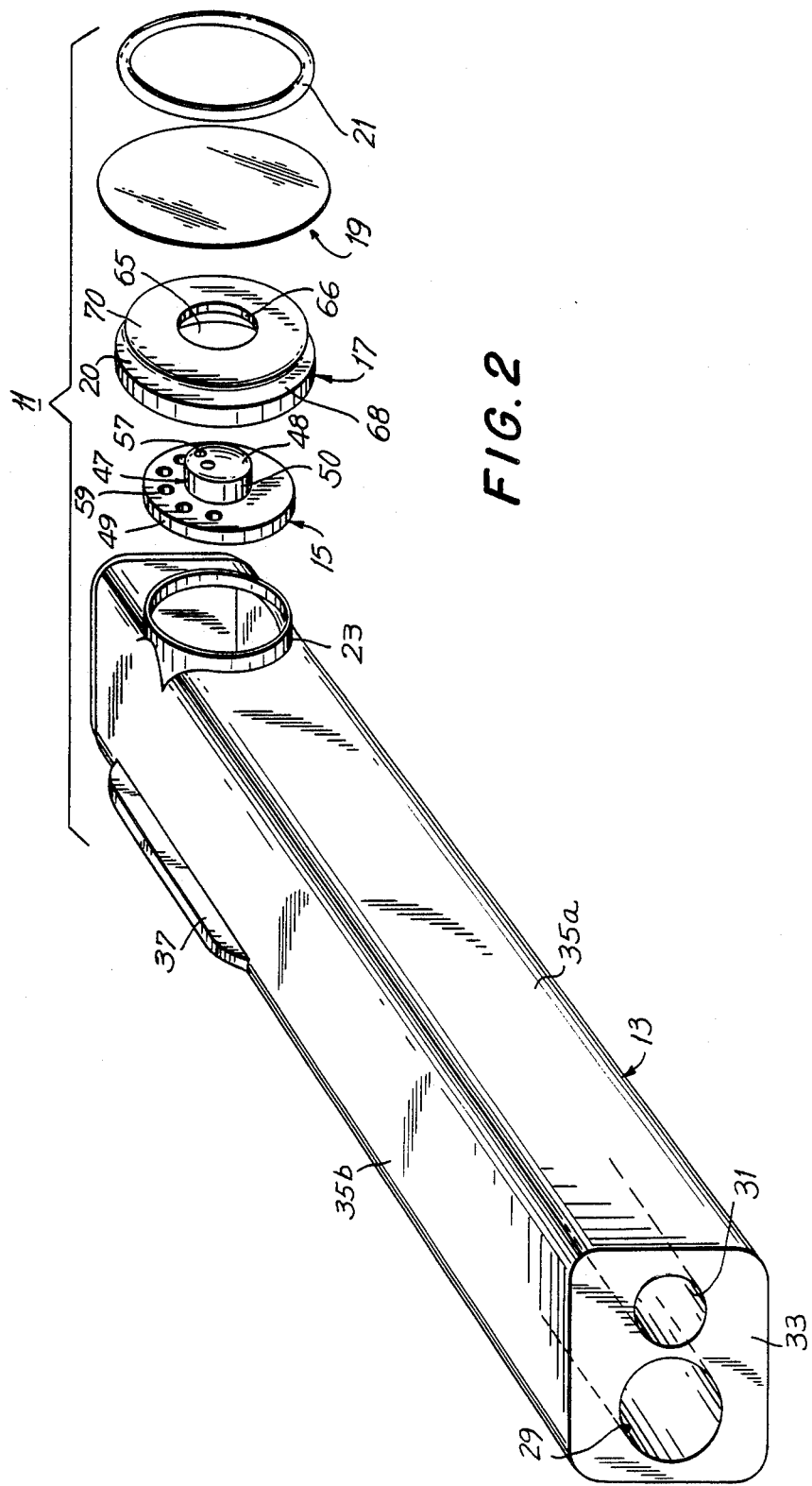

METHOD AND APPARATUS FOR MEASURING BLOOD GLUCOSE CONCENTRATION

BACKGROUND OF THE INVENTION

This invention relates to a method and apparatus for measuring blood glucose concentration using glucose which is present at the buccal mucosal surface, and more particularly to an apparatus and method for measuring blood glucose concentration by means of the peroxidative enzyme glucose oxidase.

In general, an enzymatic electrode is often used to measure the level of a blood substance. A typical enzymatic electrode combines enzymatic and polarographic technologies. The enzyme is usually bound, physically or chemically, to an inert support.

Many enzymatic electrodes utilize enzymes which catalyze the peroxidative oxidation of a substrate and generate hydrogen peroxide. The specificity of the electrode is determined by the substrate specificity of the enzyme. Two types of analytical measurements are possible, each one using the polarographic technique. Specifically, either the consumption of free oxygen or the production of hydrogen peroxide may be measured. Both serve as stoichiometric indicators of substrate oxidation. When the enzyme electrode is used after it has been calibrated using known concentrations of the substrate, the electrode becomes a tool for the quantitative analysis of unknown concentrations of that same substrate.

Enzymatic peroxidation requires two substrates: oxygen, which is usually present in excess, and the unknown, for which the enzyme is specific and which is usually present in a limited amount. In operation, the enzyme is placed in an oxidized state before reacting with a substrate. Then, after enzyme-substrate interaction, the enzyme is reduced. This reduced enzyme is re-oxidized in order to produce hydrogen peroxide. If oxygen were not present, the catalytic enzyme cycle would be inhibited.

In view of the above, it is desirable to provide an enzyme electrode apparatus for the analysis of glucose in an animal or human using the enzyme glucose oxidase. Such a device would be very useful in a program of diabetes management, relieving the diabetic of the need to obtain blood samples for glucose analysis.

In order to determine blood glucose concentration for diagnostic and other purposes, the present state of the art requires that blood samples be obtained. In a patient, samples are usually obtained either by pricking the finger or by intravenous withdrawal. However, these invasive methods are not satisfactory since tissue damage and patient discomfort often result.

A glucose oxidase-containing enzyme electrode apparatus has been previously constructed which is suitable for intravenous implantation. Such an apparatus, however, is not fully satisfactory since fibrous tissue growth and immune system rejection may inhibit proper functioning of the apparatus over long periods of time.

As a non-invasive alternative, the measurement of blood glucose concentration at a body surface may be used. This is achieved without the necessity of obtaining a blood sample. Body surface areas that may be suitable include the skin and the mucous membranes.

It is generally known that glucose diffuses from subdermal capillaries onto the surface of hydrated skin. This was shown by experiments which consisted of placing drops of buffer solution (which contained enzymes and coenzymes used in the enzymatic analysis of glucose) onto the skin, and then measuring the increase in fluorescence as NADP was reduced to NADPH. Significantly, although dry skin is an effective barrier to the diffusion of hydrophilic molecules such as glucose, that barrier is reduced by the removal of keratinizized layers, thereby leaving only the dermis. However, the buccal mucosa and the dermis have nearly identical diffusion characteristics for many hydrophilic molecular species, including glucose.

Accordingly, it is an object of the present invention to provide a method for measuring blood glucose concentration using glucose which is present at the buccal mucosal surface of a living being.

It is another object of the present invention to provide a method for measuring blood glucose concentration by means of the peroxidative enzyme glucose oxidase.

Still a further object of the present invention is to provide a method for measuring blood glucose concentration which is non-invasive.

Yet another object of the present invention is to provide a method of measuring blood glucose concentration using an excess oxygen supply.

It is still a further object of the present invention to provide a method of measuring blood glucose concentration by means of an electrode apparatus.

Still other objects of the invention will in part, be obvious, and will, in part, be apparent from the following description.

SUMMARY OF THE INVENTION

Generally speaking, in accordance with the invention, a method of measuring blood glucose concentration using glucose which is present at a mucosal surface of a living being is provided. The method includes the steps of positioning a glucose oxidase membrane on the mucosal surface, providing oxygen to the surface in order to peroxidatively oxidize the glucose and produce hydrogen peroxide as a product, electrically measuring the amount of hydrogen peroxide produced, and calibrating the measured amount of hydrogen peroxide in order to determine blood glucose concentration.

The method can be achieved by using an electrode apparatus which supports a glucose oxidase membrane at one end and which supplies oxygen to the region of the membrane, either from the atmosphere or from the air in the orifice containing the mucosal surface. The membrane is placed against the mucosal surface of the living being in order to initiate a peroxidative oxidation reaction. Then, by means of electrodes in communication with the membrane, the amount of hydrogen peroxide produced during peroxidative oxidation is electrically measured and calibrated in order to determine blood glucose concentration.

In the preferred embodiments, glucose concentration is measured at the buccal mucosal surface.

The invention accordingly comprises the several steps and the relation of one or more of such steps with respect to each of the others, and the apparatus embodying the features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is made to the following description taken in connection with the accompanying drawings, in which:

FIG. 2 is an exploded perspective view showing the apparatus of FIG. 1 in accordance with the invention;

DETAILED DESCRIPTION OF THE PREFERRED EMBODIMENT

In order to measure diffused glucose at the buccal mucosal surface by means of peroxidative oxidation, an adequate oxygen supply is needed. However, the oxygen concentration found in the buccal mucosal is normally inadequate to support peroxidative oxidation. In accordance with the invention, the oxygen deficiency is overcome by providing an electrode apparatus in which the components are arranged so that oxygen is transmitted to a membrane/electrode interface. Consequently, when placed in an oxygen-deficient environment, such as on the buccal mucosal surface, an oxygen concentration gradient is formed in order to drive oxygen into and through the membrane which covers the face of the electrode.

Figure 4:
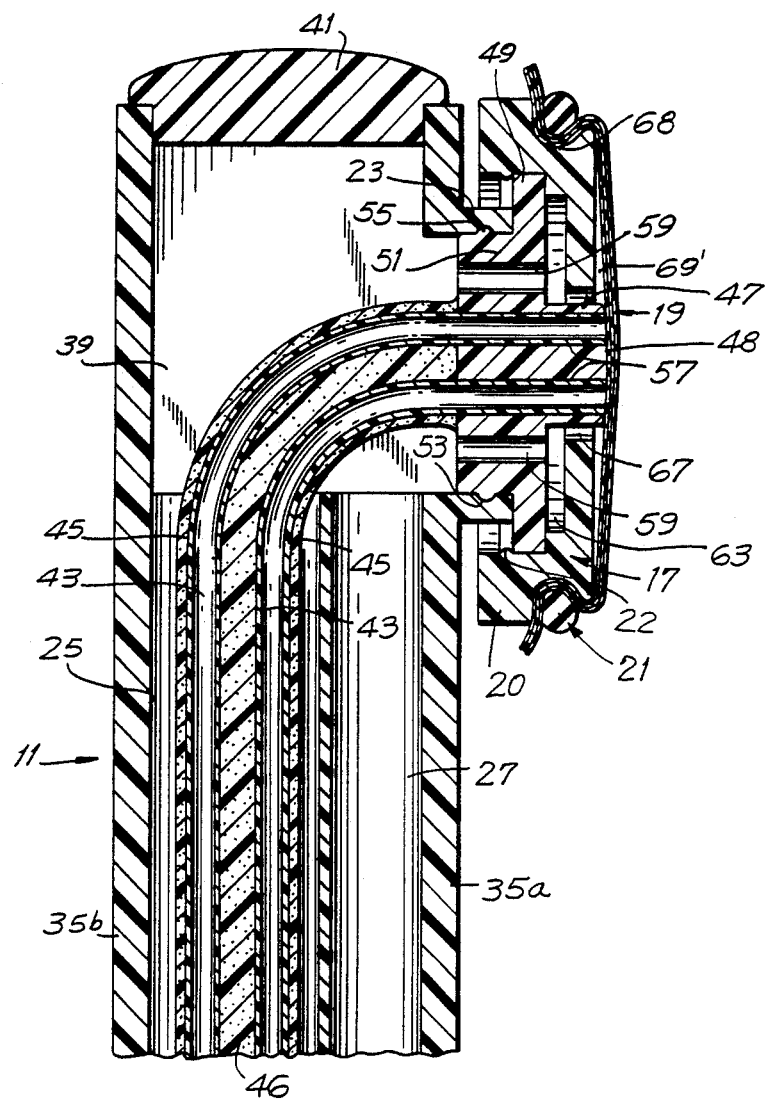
FIG. 4 is a cross-sectional view of the apparatus of FIG. 1 in accordance with the invention and illustrates the oxygen pathway and electrode wire pathway disposed therein.

Referring first to FIGS. 2 and 4, an electrode apparatus 11 in accordance with the invention is shown. Apparatus 11 includes a handle 13, an electrode holder 15, a cap member 17, a membrane member 19 and an O-ring 21.

Figure 3:
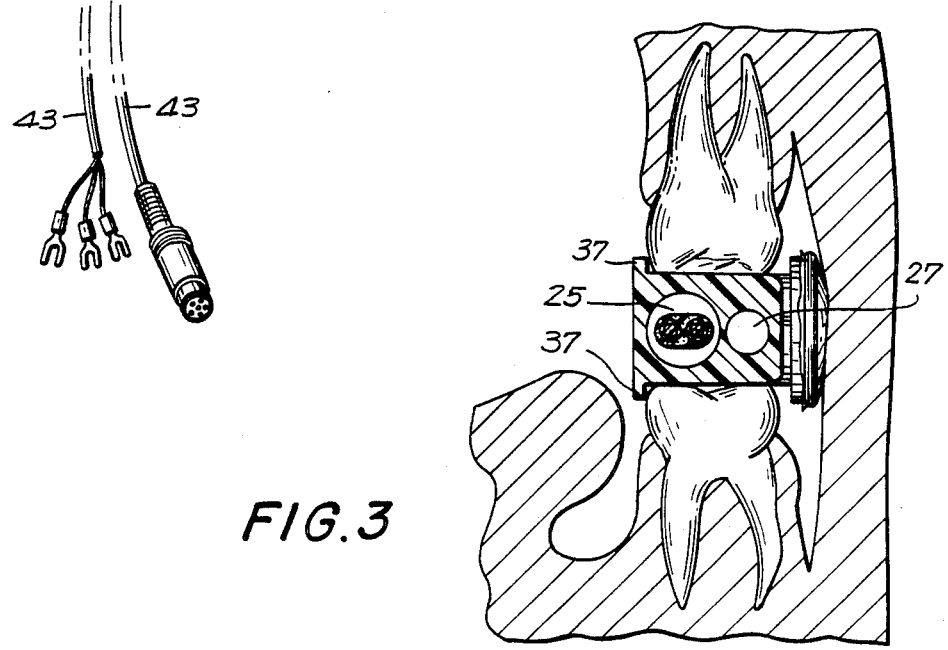
FIG. 3 is a cross-sectional view taken along line 3—3 of FIG. 1.

Handle 13 of apparatus 11 is substantially tubular in shape and has a top member 41, a bottom 33, and four sides 35a–d. As shown in FIGS. 2 and 3, handle 13 also includes ridge members 37 extending laterally from side 35c adjacent top member 41. During use of the apparatus, ridge members 37 abut the lingual surface of the teeth to hold apparatus 11 securely in position in the mouth.

Handle 13 also includes a cylindrical housing side arm 23 on side 35a proximate top member 41. Side arm 23 receives electrode holder 15 during assembly of apparatus 11, as best shown in FIG. 2.

Referring once again to FIGS. 2 and 4, handle 13 is formed with an electrode wire pathway 25 and an air pathway 27 longitudinally disposed therein. Electrode wire pathway 25 communicates with the outside by means of an electrode wire opening 29 formed in bottom member 33. Electrode wire pathway 25 houses a plurality of electrode wires. In the preferred embodiment, as shown in FIG. 4, two wires 43 are illustrated, one of which is made of platinum and the other of which is made of silver. Each wire 43 is provided with a conventional insulating material 45 therewith. An additional insulating material 46, which is preferably a Teflon shrink tubing, but which alternatively may be an epoxy resin, may be used within wire pathway 25.

Air pathway 27 communicates with the outside by means of an air opening 31 formed in bottom member 33. The other end of air pathway 27 is in communication with an air space 39 formed below top member 41 of handle 13.

As best illustrated in FIG. 2 and FIG. 4, electrode holder 15 of apparatus 11 is detachably receivable in side arm 23 of handle 13 and includes a plug portion 51, a disc portion 49 integrally formed therewith and a central pillar 47 extending from disc portion 49 opposite plug portion 51. Pillar 47 includes a face 48 and a cylindrical wall 50, both of which are preferably fabricated of or coated with a non-wettable material, such as Teflon. In order that holder 15 can be readily received in and retained by side arm 23, plug portion 51 of holder 15 is preferably formed with a circumferential ridge 55 which matingly engages circumferential groove 53 disposed along the inside of side arm 23.

Holder 15 is formed with centrally positioned orifices 57 for receiving electrode wires 43. Orifices 57 extend through pillar 47, including face 48 thereof. During assembly, electrode wires 43 are inserted into wire opening 29 of bottom member 33, through wire pathway 25 of handle 13, outside arm 29 and into orifices 57.

Holder 15 is also formed with a plurality of circumferentially positioned air orifices 59. Orifices 59 extend through plug portion 51 and disc portion 49 of holder 15, but do not extend through and are circumferentially positioned with respect to pillar 47, preferably, as shown best in FIG. 2, in a semi-circular arrangement. This construction is advantageous since it enables uniform diffusion of oxygen to the membrane surface when the apparatus of the invention is operatively positioned on the buccal mucosal of a living being. Orifices 59 communicate with air space 39 of handle 13 so that air which enters air space 39 from air channel 27 can pass therethrough.

As shown in FIGS. 2 and 4, cap member 17 of apparatus 11 includes a central cut-out 65, an annular face 70, a circumferential groove 68 and a protruding annular lip 20. Lip 20 includes a circumferential rib 22 which engages the rim of disc portion 49 when cap member 17 is attached to holder 15. Cut-out 65 includes an internal wall 66 which is preferably fabricated of or coated with a non-wettable material, such as Teflon. Cap member 17 is attached to and matingly engaged with holder 15 such that central pillar 47 of holder 15 projects through cut-out 65, as FIG. 4 illustrates.

Once cap member 17 is attached to holder 15, an annular interior space 63 is formed therebetween which communicates with air orifices 59 of holder 15. Moreover, since cut-out 65 has a diameter larger than the diameter of pillar 47, a circumferential air chamber 67 is formed around pillar 47 which communicates with interior space 63. By this construction, air in air space 39 will pass through air orifices 59 in holder 15, then enter interior space 63 and finally pass into circumferential air chamber 67.

Figure 7:
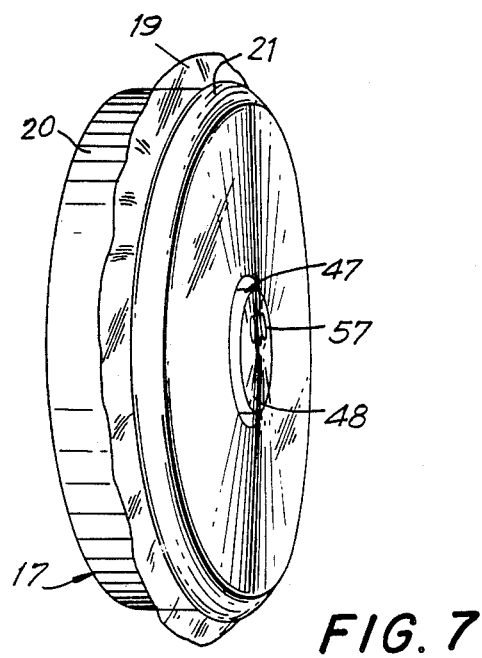
FIG. 7 is a perspective view showing the membrane attached to the cap member of the apparatus.

Referring now to FIG. 7, membrane member 19 of apparatus 11 is stretchingly fit across cap member 17. This is achieved by positioning the perimeter of membrane member 19 along circumferential grove 68 of cap member 17 and then fitting elastic O-ring 21 thereabout. Moreover, since pillar 47 projects beyond cap member 17, forcing membrane member 19 to assume a somewhat convex shape, an annular aqueous reservoir 69' is formed between membrane member 19 and cap member 17. Because membrane member 19 must be maintained in a physiological isotonic solution, or alternatively in a preservative liquid, when the apparatus of the invention is not being used, reservoir 69' becomes filled with that liquid and remains filled with that liquid when the device is operatively positioned on the buccal mucosal surface of the user. Accordingly, air which enters the apparatus through the various air pathways previously described will ultimately pass into aqueous reservoir 69' and contact membrane member 19. As a result, a sufficient oxygen supply is provided for the peroxidative oxidation reaction in membrane member 19.

Referring again to FIGS. 4 and 7, after attaching membrane member 19 to cap member 17, face 48 of pillar 47 abuts membrane member 19 such that electrode wires 43 contact membrane member 19. Moreover, since face 48 is rounded, membrane member 19 is retained snugly and smoothly against face 48.

Figure 5:
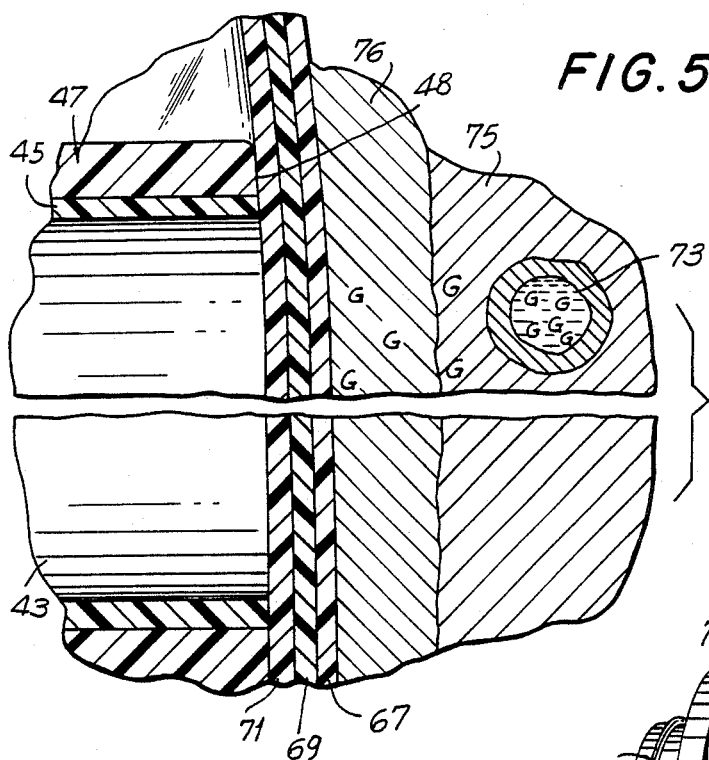
FIG. 5 is an enlarged cross-sectional view of a portion of the apparatus shown in FIG. 4 and shows in detail the 3-layer membrane and electrode of the apparatus.

Referring now to FIG. 5, membrane member 19 preferably comprises three layers: an outermost protective layer 67, a central glucose oxidase layer 69, and an inner limiting membrane layer 71. Outermost layer 67 extends along the entire surface of cap member 17, and is preferably made of cellulose. Layer 67 serves to stabilize membrane member 19 since it is the thickest and strongest of the three layers. Layer 67 also serves to exclude all substances having a molecular weight greater than 3500, while offering little resistance to molecules of a much lower molecular weight.

Central layer 69 is not coextensive with outermost layer 67, but extends only along face 48 of pillar 47. Layer 69 contains covalently-immobilized glucose oxidase and may be made of any material which has free reactive groups suitable for attaching the glucose oxidase molecules. Preferably, a natural membranous material which has free —$NH_2$ groups, such as bovine mesentery (obtainable from a slaughter house or butcher shop), is used. In preparing the central layer 69, the membranous material is first incubated with glucose oxidase and the coupling reagent glutaraldehyde (which both attaches the enzyme to the membrane and crosslinks residual membrane —$NH_2$ groups). Layer 69 is then extensively washed and dried. Thereafter, layer 69 is rehydrated before use with the invention.

Layer 69 occupies an area overlying electrode wires 43 at their tips. In the preferred embodiment, glucose diffuses through outer membrane layer 67 from the buccal mucosal surface, while oxygen diffuses across inner layer 71, which is positioned between layer 69 and pillar 47 of holder 15. Glucose oxidase catalyzes the following reaction:

Inner membrane layer 71 is made preferably of cellulose acetate by means of a cast film, and prevents the passage of molecules having a molecular weight greater than 100. Hydrogen peroxide, which is a product of the glucose oxidase catalyzed reaction, diffuses through membrane layer 71 to electrode wires 43, where it is detected polarographically, yielding a current proportional to concentration as a result of the following reaction:

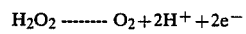

Figure 1:
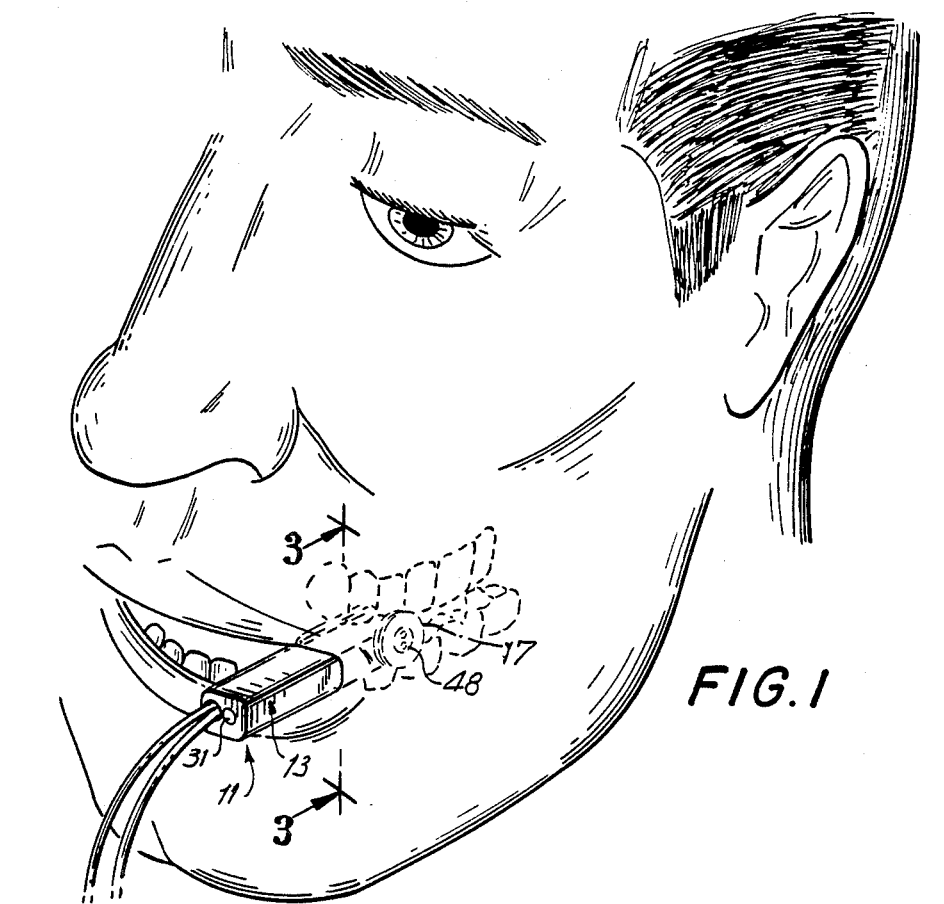
FIG. 1 is a schematic view, partially in phantom, showing an apparatus in accordance with the invention inserted within the mouth of the user.

Turning now to FIGS. 1, 3, and 5, apparatus 11 is illustratively shown in FIG. 1 operatively positioned in the mouth of a human user. Cap member 17, which has membrane member 19 disposed thereover, is placed on the rinsed buccal mucosal surface. As shown schematically in FIG. 5, glucose molecules G diffuse from a subdermal capillary 73 through interstitial tissue 75 and mucosal tissue 76 to membrane member 17 along a concentration gradient. The presence of excess oxygen in the region of membrane member 17 enables the peroxidative oxidation reaction to take place with glucose as the limiting factor. Accordingly, the concentration of hydrogen peroxide produced bears a direct stoichiometric relationship to the concentration of glucose which was initially present.

Electrode wires 43, which extend through the device and contact membrane member 19, transmit an electrical signal when apparatus 11 is operatively placed on the buccal mucosal surface. Specifically, the presence of hydrogen peroxide, the product of peroxidative oxidation, is detected polarographically by electrode wires 43. This is achieved by the platinum electrode wire detecting the negative potential (electron migration) produced by the reaction. The strength of the signal generated is proportional to the concentration of hydrogen peroxide produced and the wires transmit the electrical signal to an external device (a readout means) which amplifies the signal and displays and records changes in concentration as a function of time. Significantly, since membrane member 19 is pliable, it adheres tightly to face 48 of pillar 47 so that no gap is formed between face 48 and membrane member 19 which would otherwise inhibit peroxide diffusion towards wires 43.

Figure 6:
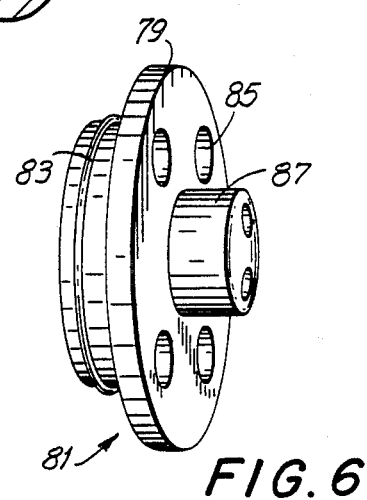
FIG. 6 is a perspective view showing an alternate embodiment of the electrode holder of the apparatus.

Reference is now made to FIG. 6, which illustrates a second embodiment of the electrode holder, generally designated at 81, in accordance with the invention. Holder 81 includes a disc portion 79 and a plug portion 83 integrally formed therewith. Holder 81 also includes a pillar 87 which projects opposite plug portion 83. In this embodiment, holder 81 includes a plurality (four) of holes 85 disposed at equally spaced intervals about the circumference. This construction is also advantageous since it enables uniform diffusion of oxygen to the membrane surface.

In general, the handle of the apparatus has the following functions:

1. It serves as a conduit for the transmission of air to the interior of the holder.

2. It contains the wiring through which electrode polarization is transmitted and from which a current, proportional in intensity to the glucose concentration at the mucosal surface, is sent to amplifiers and then to a display device. The electronic functions may be contained within the handle or may be located in a separate unit connected by wires to the handle.

3. It stabilizes the electrode apparatus when in position against the buccal mucosal surface. Stability is maintained by a ridge, running lengthwise on the top and bottom of the handle, which is placed tightly against the lingual margin of the teeth. This stabilization eliminates non-glucose related signals, which may be caused by the physical movement of the device after electrode-buccal contact has been made, or by the intrusion of saliva.

The electrode holder serves the following functions:

1. It permits the flow of oxygen from the electrode housing into the space between the electrode holder and the cap member.

2. It provides a watertight, insulated housing for the connecting wiring and working electrode surfaces which are used to detect the hydrogen peroxide product of the enzymatic reaction.

The oxygen-transmitting glucose electrode apparatus in accordance with the invention yields steady-state signals wherein the amount of glucose measured at the buccal mucosal surface equals the amount of glucose in the capillaries minus the amount taken up by the cells in transit from the capillaries to the buccal mucosal surface. At a steady state, the glucose concentration at the buccal mucosal surface equals that of the interstitial fluid which bathes the living cells. Therefore, these signals in turn can be correlated with blood glucose under both preprandial and glucose tolerance test conditions.

During operation, between 5 and 10 minutes is required for the glucose-related signal to attain a steady-state level. At this steady-state level, the glucose concentration equilibrium between the membrane and the buccal mucosal surface is achieved. Maintaining a constant contact, however, between the electrode face and the mucosal surface for that time period is difficult and requires training. Accordingly, since the relationship between the initial rate of an enzyme-catalyzed reaction, at a given temperature, and the concentration of substrate is well known, that relationship may be substituted for a steady state analysis. Thus, the initial rate of change of the electrode signal is preferably used to indicate buccal glucose concentration.

The electrode of the inventive apparatus may be calibrated at room temperature (25 degrees Celsius), using known concentrations of glucose.

Specifically, when the apparatus of the invention is placed operatively on the buccal surface, the face of the electrode may be warmed by contact with the body. Since the rate of an enzyme-catalyzed reaction is temperature-dependent, measurements of temperature are made (such as by a thermistor), both in vitro and in vivo, to allow calibration and analysis at known temperatures. This allows the user to calibrate the electrode at any temperature within 20-40 degrees Celsius (68-104 degrees Fahrenheit), and then to measure buccal mucosal glucose concentration at any other temperature within this range, multiplying the measured amperage by a constant in order to compensate for the effect of temperature. The rate at which the electrode-membrane interface comes to thermal equilibrium after being placed on the buccal mucosal may also be measured.

In accordance with the invention, an output signal is produced which increases in proportion to the amount of glucose present at the mucosa. Both the rate at which the signal increases and the steady state which is ultimately obtained are directly proportional to the concentration of glucose in the capillaries.

As soon as the membrane is applied to the buccal mucosa, a concentration gradient for oxygen is formed (this gradient can range between approximately 8.6 mM in the air and about 0.2 mM at the interface). Consequently, oxygen from the atmosphere is conducted through the oxygen pathway of the apparatus to the membrane retained against the buccal mucosal surface. The electrode system thus uses the atmosphere as a reservoir to supply oxygen for the peroxidative enzymatic reaction at the membrane-electrode interface.

The principles embodied in the present invention extend beyond glucose analysis to all applications involving the use of oxygen-requiring enzyme electrodes in oxygen-deficient environments.

After the membrane is placed over the electrodes, each electrode is calibrated by first immersing the membrane in a physiological buffer solution and then adding aliquots of Beta-D-glucose. The current from the electrodes increases in proportion to increasing glucose concentration.

The presence of glucose at the buccal surface is analyzed after each subject first rinses his mouth thoroughly with distilled water to cleanse the mouth of surface glucose, including salivary glucose. Thereafter, an abrasive material (such as a piece of gauze) is used to wipe the surface to which the membrane is to be applied in order to remove mucosal residue and other contaminants. Placement of the membrane onto the buccal mucosal yields a current which increases to a plateau level over a time interval of about 5 minutes.

Figure 8:
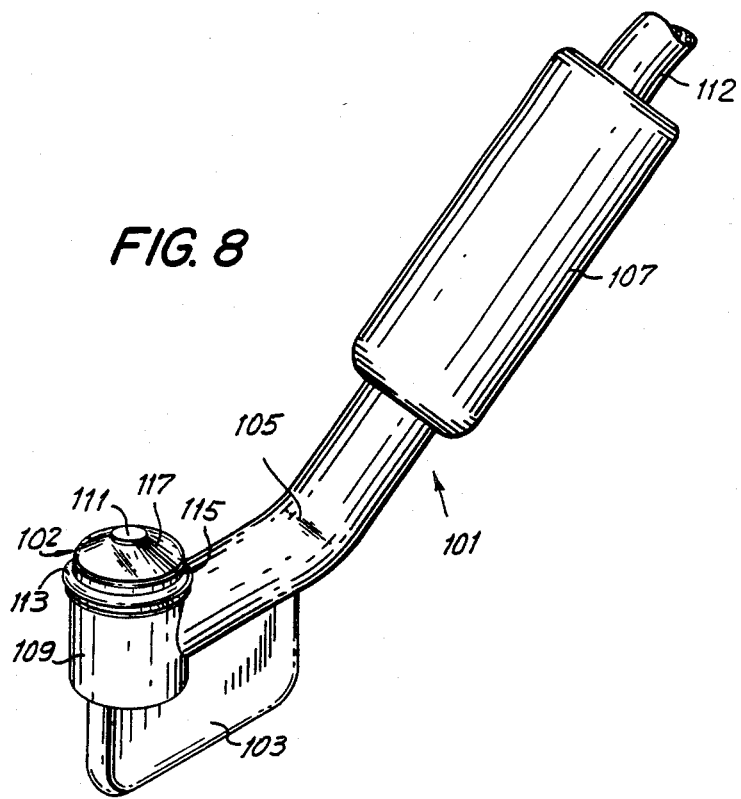
FIG. 8 is a perspective view of an alternate embodiment of the apparatus in accordance with the invention.
Figure 9:
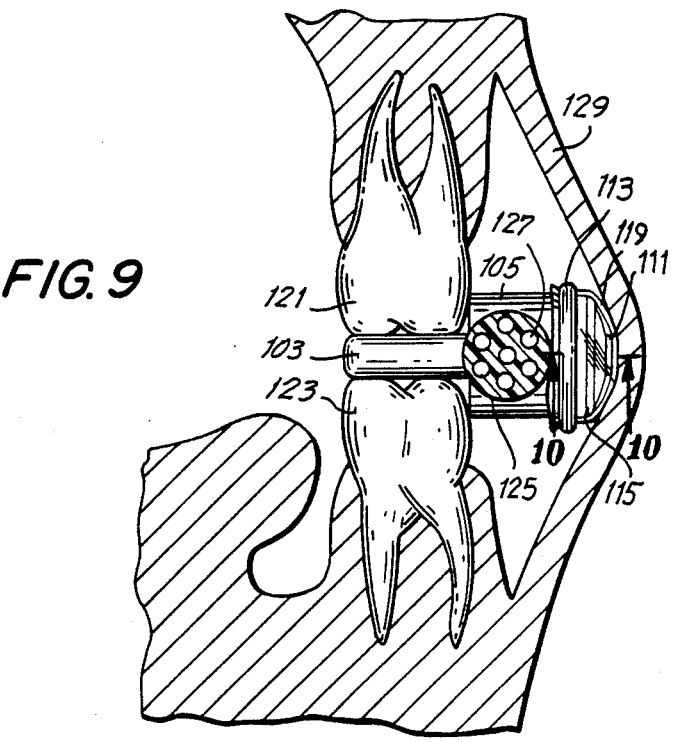
FIG. 9 is a side view in partial cross-section, showing the electrode apparatus of FIG. 8 positioned within the mouth of the user and held in place by the user's teeth.

Referring now to FIGS. 8 and 9, an electrode apparatus 101 in accordance with a second embodiment of the invention is shown. Apparatus 101 includes a handle 107, a stem 105 connected to handle 107, a base member 109, and an electrode or probe member generally designated at 102 supported by base member 109. Apparatus 101 also includes a ridge member 103 extending laterally from base member 109 and stem 105. During use of apparatus 101 in the mouth of the user, as best shown in FIG. 9, ridge member 103 is securely gripped between the user's upper molar 121 and lower molar 123 in order to hold apparatus 101 securely in position in the mouth.

Apparatus 101 is formed with an electrode wire pathway 125 longitudinally extending through handle 107 and stem 105. Electrode wire pathway 125 communicates with the outside by means of an electrode wire opening (not shown) formed at one end of handle 107. Electrode wire pathway 125 receives and houses an electrical cable 112 containing a plurality of electrical wires 127. Electrical wires 127 extend through apparatus 125 and can transmit an electrical signal when apparatus 101 is operatively placed on the buccal mucosal surface of a patient's mouth.

Figure 10:
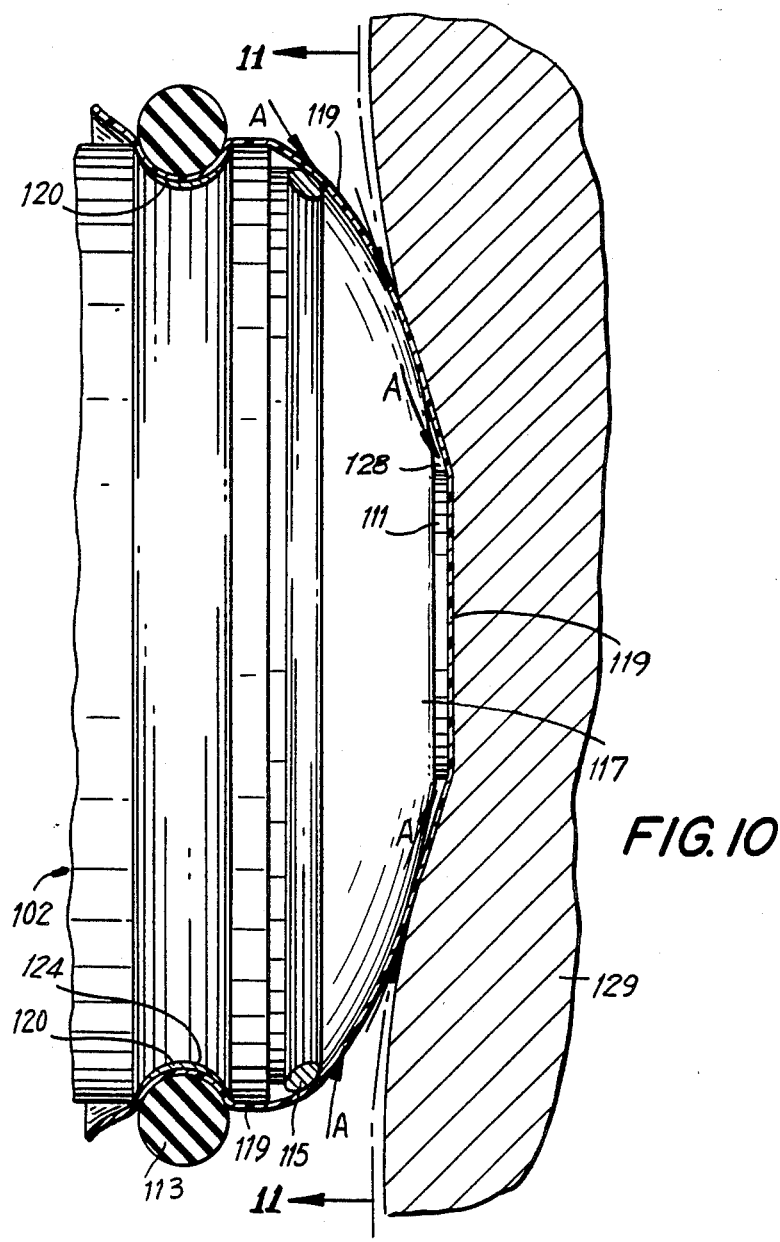
FIG. 10 is a cross-sectional view taken along line 10—10 of FIG. 9, showing the probe tip of the electrode apparatus in contact with the buccal mucosa.

Turning now to FIG. 10, electrode member 102, which is supported by base member 109, is shown in contact with the buccal mucosa 129 of a patient's mouth. Electrode member 102 includes a face region 117 and an anode 111, preferably made from platinum, centrally positioned on face 117 and protruding slightly therefrom. Electrode member 102 also includes a substantially annular cathode 115 preferably made of silver and disposed substantially along the peripheral region of face 117. Anode 111 and cathode 115 are electrically connected to electrical wires 127 inside electrode member 102 (not shown).

Figure 12:
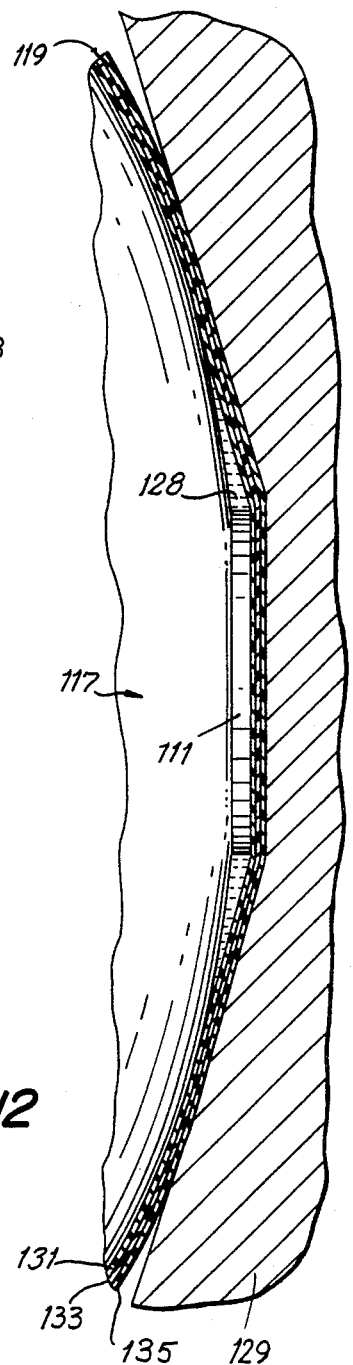
FIG. 12 is an enlarged cross-sectional view taken along line 12—12 of FIG. 11.

A membrane member 119 of apparatus 101 is stretchingly fit across face 117 of electrode member 102. This is achieved by positioning the perimeter of membrane member 119 along circumferential groove 124 of electrode member 102 and then fitting an elastic O-ring 113 thereabout. Since anode 111 protrudes beyond face 117, thereby forcing membrane member 119 to assume a somewhat convex shape, an annular gap 128 is formed between membrane member 119 and face 117, as best shown in FIGS. 10 and 12. Moreover, annular cathode 115 protrudes somewhat beyond the periphery of face 119 and also contacts membrane member 119.

Optionally, electrode member 102 includes a reference electrode 120 which is positioned beneath O-ring 113, as illustrated in FIG. 10. Reference electrode 120 is preferably made of platinum and has the function of increasing electrical stability; electrode member 120 is normally kept at 0 volts.

Figure 11:
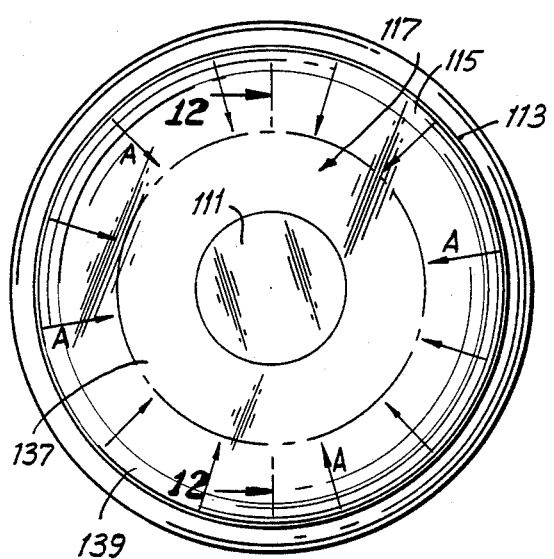
FIG. 11 is a frontal view taken along line 11—11 of FIG. 10.

Turning now to FIGS. 11 and 12, and still referring also to FIG. 10, membrane member 119 is shown operatively positioned over face 117 of electrode member 102 and abutting anode 111 and cathode 115. Membrane member 119 is preferably made from three layers: an outermost protective layer 135, a central glucose oxidase layer 133 and an inner membrane layer 131. Outermost layer 135 extends along the entire surface of electrode member 102 and is made of polycarbonate. Inner membrane layer 131, which overlies both anode 111 and cathode 115, is made of cellulose acetate. This material is chosen since it is selectively permeable and will enable diffusion of $H_2O_2$ more readily than other substances having a greater molecular weight than $H_2O_2$.

Central layer 133 contains covalently-immobilized glucose oxidase and may be made of any material which has free reactive groups suitable for attaching glucose oxidase molecules, similar to central layer 69 of the first embodiment.

Before placing apparatus 101 in the mouth of a patient, three-layer membrane member 119 is saturated with an aqueous electrolyte or buffer solution. The buffer solution then becomes saturated with atmospheric oxygen. For optimal performance, annular gap 128 formed between membrane member 119 and face 117 is filled with the buffer solution.

After the apparatus is placed in the patient's mouth, the central region of membrane member 119 contacts bucccal mucosa 129, as shown in FIG. 10. However, the peripheral region of membrane member 119 does not contact the buccal mucosa, but remains in communication with the air in the patient's mouth. Because of the glucose oxidase reaction which occurs in the region of membrane member contact with the buccal mucosa, the oxygen level in the buffer solution which has saturated membrane member 119 decreases. As a result, oxygen will diffuse from the air in the patient's mouth through the peripheral region of membrane member 119 and toward the central region of membrane member 119, as arrows A in FIGS. 10 and 11 illustrate.

Consequently, an oxygen gradient is formed in membrane member 119, and can be characterized as the difference between the oxygen concentration in the saturated buffer solution (approximately 0.21 mM) at the periphery and that at the buccal mucosa (approximately 0.08 mM to 0.13 mM). This enables a sufficient quantity of oxygen to be supplied to the buccal mucosal region in order to peroxidatively oxidize all of the glucose present thereat, and thereby produce hydrogen peroxide as a product.

In operation, electrode wires 127, which extend through apparatus 101, and which are electrically connected to cathode 115 and anode 111, as well as to reference electrode 120, transmit an electrical signal when electrode member 102 is operatively positioned on the buccal mucosal surface. More particularly, the presence of hydrogen peroxide, the product of peroxidative oxidation, is detected polarographically by cathode 115 and anode 111, and is transmitted along electrode wires 127 to an external device (a readout means) which amplifies the signal and displays and records changes in concentration as a function of time. Electrical detection of hydrogen peroxide is similar to detection in the first embodiment of the electrode apparatus.

Electrode apparatus 101, however, has certain advantages over the first embodiment. Specifically, its sensitivity is at least five times greater, the noise level is reduced at least ten times and the signal to noise ratio is increased at least fifty times. This is because of the following structural and functional changes:

1. a substantial increase in electrode surface area;
2. the inclusion of a third electrode surface —the reference electrode;
3. supplying oxygen from the air within a patient's mouth to the mucosal surface;
4. a unique three-layer membrane member which includes glucose oxidase in the central layer and which substantially inhibits the diffusion of various undesirable substances to the surface of the anode;
5. increased stabilization of the position of the electrode and membrane against the buccal mucosal; and
6 a reduction in the size and weight of the electrode apparatus.

Although the method in accordance with the invention preferably includes measuring hydrogen peroxide production in order to determine glucose concentration, the method can alternatively include measuring oxygen loss in order to determine glucose concentration. This may be achieved by reversing the polarity of the electrodes and measuring the decrease in current as molecular oxygen is reduced to peroxide.

Even though the method described herein is for measuring blood glucose concentration using glucose which is present at the buccal mucosal, the method is suitable for measuring blood glucose concentration using glucose which is present at other mucosal surfaces such as the rectal, vaginal and nasal mucosal surfaces of a living being.

Although an electrode apparatus in accordance with the invention does not include a readout means, a readout means for interpreting the electrical signals carried along the wiring may be part of the apparatus.

It will thus be seen that the objects set forth above, among those made apparent from the preceding descriptions are efficiently attained and, since changes may be made in carrying out the above method and in the construction of the apparatus set forth, without departing from the spirit and scope of the invention, it is intended that all matter contained herein shall be interpreted as illustrative and not in a limiting sense.

It is also understood that the following claims are intended to cover all the generic and specific features of the invention found herein and all statements of the scope of the invention which, as a matter of language, might be said to fall there-between.

We claim:

1. An apparatus suitable for use in measuring blood glucose concentration in a living being using glucose which is present at the buccal mucosal surface of said being, said apparatus comprising:

membrane means for containing glucose oxidase enzyme;

means for positioning the said membrane means against said buccal mucosal surface;

means for providing oxygen for said membrane means, said provided oxygen used for peroxidative oxidation of said glucose when said membrane means is positioned against said mucosal surface, said oxidation yielding hydrogen peroxide as a product; and means for measuring in said membrane means changes in the concentration of at least one compound selected from the group including said provided oxygen and said hydrogen peroxide product.

2. The apparatus of claim 1, wherein said measuring means comprises electrode means for generating a signal proportional to changes in the concentration of said at least one compound.

3. The apparatus of claim 2, wherein said electrode means includes wire means for transmitting said signal.

4. The apparatus of claim 3, wherein said positioning means comprises a handle member, a holder member connected to said handle member and cap member connected to said holder member, said membrane means being stretchingly fit across the face of said cap member.

5. The apparatus of claim 4, further including a first wire pathway disposed in said handle member and a second wire pathway disposed in said holder member, and wherein said wire means is housed within said first and second wire pathways.

6. The apparatus of claim 5, wherein said holder member includes a pillar extending opposite from said handle member when said holder member is connected to said handle member, said pillar including said second wire pathway.

7. The apparatus of claim 6, wherein said cap member includes a central cutout, and wherein said pillar of said holder member projects through said cutout when said cap member is connected to said holder member.

8. The apparatus of claim 7, wherein said pillar extends beyond said cap member when said cap member is connected to said holder member, said pillar including a face which abuts against said membrane means stretchingly fit over said cap member, whereby said wire means contacts said membrane means at said face for transmitting said signal.

9. The apparatus of claim 2, wherein said electrode means comprises an anode member and a cathode member.

10. The apparatus of claim 9, wherein said electrode means further comprises an electrical grounding member.

11. The apparatus of claim 10, wherein said positioning means comprises a handle member, a stem member connected to said handle member, a base member connected to said stem member and a probe member supported by said base member, said membrane means being coveringly fit over said probe member.

12. The apparatus of claim 11, wherein positioning means further includes a ridge member extending laterally from said stem member.

13. The apparatus of claim 11, wherein said probe member includes said anode member and said cathode member.

14. The apparatus of claim 13, wherein said anode member is centrally positioned on the face of said probe member and projects beyond said probe member so as to contact said membrane means.

15. The apparatus of claim 14, wherein said cathode member is positioned along the peripheral region of said probe member.

16. The apparatus of claim 1, wherein said membrane means comprises an outer layer, a central layer and an inner layer, said outer layer being in contact with said buccal mucosal surface when said membrane means is positioned against said surface.

17. The apparatus of claim 16, wherein said outer layer comprises cellulose.

18. The apparatus of claim 16, wherein said outer layer comprises polycarbonate.

19. The apparatus of claim 16, wherein said central layer includes said glucose oxidase enzyme.

20. The apparatus of claim 16, wherein said inner layer comprises cellulose acetate.

21. The apparatus of claim 1, wherein said oxygen providing means comprises means for supplying excess oxygen to said membrane means.

22. The apparatus of claim 21, wherein said oxygen supplying means comprises means for conducting atmospheric air to said membrane means.

23. The apparatus of claim 22, wherein said positioning means comprises a handle member, a holder member connected to said handle member and a cap member connected to said holder member, said membrane means being stretchingly fit across the face of said cap member.

24. The apparatus of claim 23, wherein said conducting means includes a first pathway disposed in said handle member, a second pathway communicating with said first pathway and disposed in said holder member, and a third pathway communicating with said second pathway and disposed in said cap member.

25. The apparatus of claim 24, wherein said handle member includes means for detachably receiving said holder member.

26. The apparatus of claim 25, wherein said receiving means comprises a side arm.

27. The apparatus of claim 26, wherein said holder member comprises a plug portion received in said side arm, a disc portion and a central pillar extending from said disc portion opposite said plug portion.

28. The apparatus of claim 27, wherein said plug portion includes a ridge and said side arm includes a groove for mating engagement with said ridge.

29. The apparatus of claim 27, wherein said cap member includes a central cutout, and wherein said pillar of said holder member projects through said cutout when said cap member is connected to said holder member.

30. The apparatus of claim 29, wherein the diameter of said cutout is greater than the diameter of said pillar to form a chamber therebetween, said third air pathway comprising said chamber.

31. The apparatus of claim 24, wherein said second pathway disposed in said holder member comprises a plurality of air orifices.

32. The apparatus of claim 21, wherein said oxygen supplying means comprises means for conducting oxygen in the air of the mouth of said living being to said membrane means.

33. The apparatus of claim 32, wherein said positioning means comprises a probe member, said membrane means being stretchingly fit across the face of said probe member.

34. The apparatus of claim 33, wherein said membrane means is saturated with an electrolyte solution, said saturated membrane means comprising said oxygen conducting means.

35. A method of measuring blood glucose concentration in a living being using glucose which is present at a mucosal surface located in an orifice of said being, said method comprising:
   positioning a membrane member against said mucosal surface, said membrane member including glucose oxidase enzyme;
   providing oxygen to said membrane member to enable peroxidative oxidation of said glucose, said oxidation producing hydrogen peroxide as a product;
   measuring the change in concentration of at least one compound selected from the group including said provided oxygen and said hydrogen peroxide product; and
   calibrating said measurement in order to determine blood glucose concentration.

36. The method of claim 35, wherein said measuring step comprises measuring the amount of said hydrogen peroxide product.

37. The method of claim 35, wherein said positioning step comprises positioning said membrane member against a buccal mucosal surface.

38. The method of claim 35, wherein said providing oxygen step comprises supplying excess oxygen to said membrane member.

39. The method of claim 38, wherein said providing oxygen step comprises conducting atmospheric air to said membrane member.

40. The method of claim 38, wherein said providing step comprises conducting oxygen in the air of the mucosal orifice to said membrane member.

41. An apparatus suitable for use in measuring blood glucose concentration in a living being using glucose which is present at a mucosal surface of said being, said apparatus comprising:
   membrane means for containing glucose oxidase enzyme;
   means for positioning said membrane means against said mucosal surface;
   means for providing oxygen for said membrane means, said provided oxygen used for peroxidative oxidation of said glucose when said membrane means is positioned against said mucosal surface, said oxidation yielding hydrogen peroxide as a product; and
   means for measuring in said membrane means changes in the concentration of at least one compound selected from the group including said provided oxygen and said hydrogen peroxide product.

* * * * *